United States Patent [19]
Rose

[11] Patent Number: 6,024,949
[45] Date of Patent: Feb. 15, 2000

[54] COMPOSITIONS CONTAINING CHLOROPHYLL DERIVATIVES FOR PERMANENT WAVING OF HAIR

[75] Inventor: Burkhard Rose, Darmstadt, Germany

[73] Assignee: Goldwell, AG, Darmstadt, Germany

[21] Appl. No.: 07/928,063

[22] Filed: Aug. 11, 1992

[51] Int. Cl.⁷ ....................................................... A61K 7/09
[52] U.S. Cl. ........................ 424/70.2; 424/70.1; 424/70.5; 424/74
[58] Field of Search ................................. 424/71, 70, 47, 424/70.1, 70.2, 70.5, 74

[56] References Cited

U.S. PATENT DOCUMENTS

| | | | |
|---|---|---|---|
| 4,115,549 | 9/1978 | Scott | 424/70 |
| 4,898,899 | 2/1990 | Isobe | 524/90 |
| 4,906,462 | 3/1990 | Miki | 424/76.1 |
| 5,122,418 | 6/1992 | Nakane | 424/47 |

FOREIGN PATENT DOCUMENTS

| | | |
|---|---|---|
| 5929513 | 3/1981 | Japan. |

OTHER PUBLICATIONS

*The Merck Index*, p. 274–275 (1976).

*Primary Examiner*—Thurman K. Page
*Assistant Examiner*—Lakshmi Channavajjala
*Attorney, Agent, or Firm*—Birch, Stewart, Kolasch & Birch, LLP

[57] ABSTRACT

Composition for permanent waving of human hair comprising an at least partly water-soluble chlorophyll or chlorophyll derivative, especially an alkali magnesium or copper chlorophyllin to improve the waving performance of the composition.

7 Claims, No Drawings

COMPOSITIONS CONTAINING CHLOROPHYLL DERIVATIVES FOR PERMANENT WAVING OF HAIR

This invention refers to a composition for permanent waving of human hair, i.e. a permanent waving composition presenting improved waving properties.

It is well known that a permanent waving procedure requires two working steps: (a) reductive splitting of the cystine disulfide bonds of the hair by the action of a reducing agent, and (b) subsequent neutralization by the application of an oxidizing agent, whereby the cystine disulfide bonds are re-instated.

As already disclosed in German patents 948 186 and 972 424, the conventional reducing agent used therefor is thioglycolic acid, e.g. as an ammonium or monoethanolamine salt, which was partly replaced by glycerol monothioglycollate in recent years; however, thiolactic acid and its esters and inorganic sulfites are also used.

Thereby, compositions containing thioglycollate are prepared have a pH value within the range of approx. 7.5 to approx. 9.0, especially within 8.5 to 9.0, where alkalinization is normally effected by the admixture of ammonium (bi)carbonate (cf. e.g., U.S. Pat. No. 2,708,940.)

Permanent waving compositions based on glycerol monothioglycollate have a slightly acidic to neutral pH value.

Reducing compositions often include alkanediols or their ethers in a range from about 0.5 to about 35% by weight, preferably of about 1, particularly from about 2.5 to 15% by weight, which can also act as solvents and penetrating agents or as solubilizers or carriers.

However, these compositions still require improvement with respect to their waving performance.

It has now been found that an improved curling effect and an increased performance of permanent waving compositions can be achieved by the addition of a small quantity of chlorophyll or chlorophyll derivatives, especially of an alkali magnesium or copper chlorophyllin such as sodium or potassium magnesium chlorophyllin, preferably in a proportion of 0.01 to 0.2% by weight, especially from 0.02 to 0.1% by weight and particularly preferred from 0.025 to 0.075% by weight, calculated based on the reducing composition.

Thereby, the addition of the component is preferably made to the reducing agent containing a thio-compound or to a permanent waving pre-treatment composition before application of the reducing agent as described e.g. in DE-OS 37 40 926, or to an intermediate treatment which is applied after the processing time of the reducing agent before application of the neutralizing composition.

However, the term "permanent waving composition" according to this invention does not comprise any neutralizing preparation containing an oxidizing agent.

As mentioned above, alkali magnesium chlorophyllins, i.e. sodium and (or) potassium magnesium chlorophyllins are used as chlorophyll derivatives which are at least partly water-soluble; but other chlorophyllins may also be used wherein the magnesium atom is wholly or partly replaced by other metals, especially by copper, i.e. alkali copper chlorophyllins.

Chlorophylls made water-soluble by the addition of surfactants, are also considered as at least partly water-soluble in the sense of the invention.

A survey on suitable chlorophylls and chlorophyllins may be found in the review of J. C. Kephart in Econ. Bot. 9 (1955), pp. 3–38, "Chlorophyll Derivatives, Their Chemistry, Commercial Preparation and Uses", which is expressly referred to.

Reducing compositions are used as aqueous solutions, gels, emulsions creams, or as aerosol foams, and may contain, in addition to reducing and alkalizing agents, hair conditioning substances such as cationic polymers, thickeners, carriers to increase the penetration of the product, complexing agents, opacifiers, fragrances and also surface-active substances to improve wetting and penetration.

Preferred reducing agents in the permanent waving compositions according to this invention are particularly thioglycolic acid and ammonium thioglycollate, thiolactic acid, its salts and esters, cysteine and its hydrochloride, cysteamin, N-acetylcysteine, thio-acetic acid, its salts and esters, and especially thioglycolic acid monoglycerol ester, as well as inorganic sulfites such as sodium bisulfite. When thioglycolic acid monoglycerol ester or a similar thioester is used, it is mixed with the remaining reducing composition immediately before application.

Depending on its structure, the concentration of the applied reducing agent normally ranges between about 1 and about 15% by weight of the total reducing composition, preferably between about 3 and about 10% by weight.

The reducing composition usually includes an alkalizing agent. The quantity of the alkalizing agent depends on the reducing agent. The reducing composition preferably contains from about 1 to about 10, particularly from about 2 to about 8% by weight, of an alkalizing agent.

Suitable and preferred alkalizing agents are ammonium (bi)carbonate, ammonium carbamate, ammonia and ethanolamine. It is recommended to adjust the pH value within a range of about 7 to about 9.

The permanent waving compositions of this invention preferably include surfactants. Their proportion is set from 0.1 to about 10, especially from about 1 to about 5% by weight.

The surfactants used in these reducing compositions are preferably the known anion-active surfactants which may also be used in combination with non-ionic surfactants.

Suitable anionic surfactants are especially the well-known alkylether sulfates and carbonic acids, particularly in the form of their alkali salts, as well as protein fatty acid condensates.

Suitable non-ionic surfactants are especially $C_8$–$C_{18}$-fatty alcohol polyglycolethers, fatty acid polyglycolesters, fatty acid alkanolamide, amine oxides and, above all, $C_8$–$C_{18}$-alkyl polyglycosides.

Amphoteric surfactants may also be used, such as the well-known betaines and amido betaines as well as cation-active surfactants, e.g. quaternary ammonium compounds, particularly in cationic neutralizing compositions.

Another expedient component of the compositions according to the invention is a $C_3$–$C_6$-alkanediol or its ether, especially mono-$C_1$–$C_3$-alkyl ether.

Preferred substances in this respect are, 1,2-propanediol, 1,3-propanediol, 1-methoxypropanol(-2), 1-ethoxypropanol (-2), 1,3-butanediol, 1,4-butanediol, diethyleneglycol and its monomethylether and monoethylether, as well as dipropyleneglycol and its monomethylether and monoethylether. The proportion of these diols is preferably between about 1 to about 30, especially from about 2.5 to about 15, most preferably from about 5 to about 10% by weight of the reducing composition.

In addition to the $C_3$–$C_6$-alkanediols or their ethers, also propylene carbonate (4-methyl-1,3-dioxolane-2-one), N-alkylpyrrolidone, glycerol and urea may be used.

The compositions according to the invention may, of course, include all those ingredients which are usual in permanent waving compositions; a detailed list of the same is omitted here.

To avoid repetition, reference is rather made to the state of technology, as described in "Ullmann's Encyclopedia of Industrial Chemistry", Vol. A12 (1986), pp. 588 to 591, as well as particularly the monography of K. Schrader, "Grundlagen und Rezepturen der Kosmetika", 2. Aufl. (1989, H üthig Buch Verlag), pp. 823 to 840, and the survey paper of D. Hollenberg et al. in "Seifen-Öle-Fette-Wachse", 117 (1991), pp. 81 to 87.

To the compositions and ingredients as disclosed therein is expressly referred; they may be also used within the scope of this invention.

The following examples illustrate the invention more closely.

EXAMPLE 1

| | | Permanent waving solution for normal hair: |
|---|---|---|
| 20.00% | by wt. of | Ammonium thioglycollate, 50% |
| 2.00 | | Ammonia, 25% |
| 5.00 | | Ammonium bicarbonate |
| 1,00 | | $C_9$–$C_{11}$-Alkyl polyglycoside (condensation degree: 1.35) |
| 2.50 | | 1,3-Butylene glycol |
| 1.00 | | Non-ionic emulsifier (PEG-40 hydrogenated castor oil) |
| 0.05 | | Sodium copper chlorophyllin |
| 0.30 | | Perfume |
| @ 100.00 | | Water |

In half-head tests, this composition was applied to one side of the hair of 10 volunteers, while the other side was treated with an identical composition without chlorophyllin.

After a processing time of 15 minutes, the hair was rinsed and neutralized with a usual neutralizing solution as shown below.

After blank assessment by two hairdressers independently from each other, the volunteers treated with the compositions in accordance with example 1 presented a distinctly improved waving efficacy in comparison to the other side.

Composition of the neutralizing solution:

| | | |
|---|---|---|
| 4.80% | by wt. of | Hydrogen peroxide, 50% |
| 5.00 | | Sodium laurylether sulfate, 28% |
| 0.05 | | Phenacetin |
| 0.50 | | 1,2-Propanediol |
| q.s. | | Phosphoric acid to adjust pH to 3.0 |
| @ 100.00 | | Water |

EXAMPLE 2

| | | Permanent waving composition for dyed damaged hair |
|---|---|---|
| 16.00% | by wt. of | Ammonium thioglycollate, 50% |
| 1.00 | | Ammonia, 25% |
| 2.50 | | Ammonium bicarbonate |
| 0.50 | | $C_{10}$–$C_{12}$-alkyl polyglycoside (condensation degree 1.5) |
| 0.25 | | Cetyl trimethyl ammonium chloride |
| 0.20 | | Cationic polymer (Polyquaternium 10) |
| 0.01 | | Sodium magnesium chlorophyllin |

-continued

| | | Permanent waving composition for dyed damaged hair |
|---|---|---|
| | 1.00 | Non-ionic surfactant (PEG-40 hydrogenated castor oil) |
| | 0.30 | Perfume |
| @ | 100.00 | Water |

This composition is neutralized with a regular neutralizing composition based on hydrogen peroxide or sodium bromate.

EXAMPLE 3

| | | Foam permanent waving composition for coarse, difficult-to-wave natural hair |
|---|---|---|
| 22.00% | by wt. of | Ammonium thioglycollate, 50% |
| | 5.00 | Ammonia, 25% |
| | 4.00 | Ammonium bicarbonate |
| | 2.50 | 1,2-Propanediol |
| | 1.00 | $C_{10}$–$C_{12}$-alkyl polyglycoside (condensation degree: 1.40) |
| | 5.00 | Cocoamido propylbetaine, 30% |
| | 0.07 | Sodium copper/magnesium chlorophyllin |
| | 1.00 | Non-ionic emulsifier (PEG-40 hydrogenated castor oil) |
| | 0.40 | Perfume |
| @ | 100.00 | Water |

The hair is neutralized following a usual procedure.

EXAMPLE 4

Acidic permanent waving composition for normal to slightly damaged natural hair

Immediately before application, 25 g of glycerol monothioglycollate, 75% is added to and mixed with 75 g of a solution of

| | | |
|---|---|---|
| 0.04 g | of | Sodium magnesium/copper chlorophyllin |
| 1.00 g | | Ethylcarbitol |
| 0.10 g | | Cationic polymer (Polyquaternium-10) |
| 1.00 g | | PEG-400 hyrogenated castor oil |
| 0.50 g | | Perfume |
| 0.50 g | | Lauryl polyglycoside (condensation degree: 1.75) |
| 1.25 | | Ammonia, 25% |
| @ 75 g | | Water |

The pH value of the composition is about 6.8.

Neutralizing is effected with a regular oxidizing composition.

EXAMPLE 5

| | | Pre-treatment composition for permanent waving of normal hair, |
|---|---|---|
| 2.00% | by wt. of | 1,2-Propanediol |
| | 0.20 | Cationic polyrner (Polyquaterniuin-6) |
| | 0.10 | PEG-40 hydrogenated castor oil |
| | 0.08 | Perfurne |
| | 0.04 | Sodium copper chlorophyllin |
| | 0.05 | Citric acid |
| @ | 100.00 | Water |

EXAMPLE 6

| Pre-treatment composition for permanent waving of porous, bleached hair, | |
|---|---|
| 1.00% by wt. of | 1,2-Propanediol |
| 1.20 | Cationic polymer (Polyquaternium-10) |
| 0.10 | PEG-40 hydrogenated castor oil |
| 0.01 | Sodium magnesium chlorophyllin |
| 0.08 | Perfume |
| 0.10 | Citric acid |
| @ 100.00 | Water |

The pre-treatment composition is applied onto the hair before the reducing composition, and not rinsed after processing. After curling of the hair, the permanent waving and neutralizing procedures are effected as usual.

Hair treated with the above pre-treatment composition shows an improved waving result.

EXAMPLE 7

| Permanent waving intermediate treatment | |
|---|---|
| 10.00% by wt. of | Magnesium sulfate |
| 5.00 | 1,3-Butanediol |
| 0.05 | Sodium copper/magnesium chlorophyllin |
| q.s. | Phosphoric acid to adjust pH value to 3.5 |
| @ 100.00 | Water |

This preparation is applied to the hair after processing of the reducing agent composition and rinsing, and is not rinsed off before the end of the neutralizing procedure.

The result is a distinctly improved permanently waved hair.

I claim:

1. A composition for the permanent waving of human hair, comprising a permanent waving effective amount of a reducing agent and 0.01 to 0.2% by weight, calculated based on the total composition, of a chlorophyll or chlorophyll derivative which is at least partially water-soluble.

2. The composition according to claim 1, wherein said composition contains 0.02 to 0.1% by weight of said chlorophyll or chlorophyll derivative, calculated based on the total composition.

3. The composition according to claim 1, wherein said chlorophyll or chlorophyll derivative is selected from the group consisting of an alkali magnesium chlorophyllin, an alkali copper chlorophyllin, and mixtures thereof.

4. A method for improving the waving performance of reducing compositions for the permanent waving of human hair, comprising adding an amount of at least partly water-soluble chlorophyll or chlorophyll derivatives to a reducing composition comprising a permanent waving effective amount of a reducing agent, such that said chlorophyll or chlorophyll derivative is present in an amount of 0.01 to 0.2% by weight, calculated based on the total composition.

5. A method for the permanent waving of human hair, comprising applying a permanent waving effective amount of a permanent waving composition comprising a reducing agent and 0.01 to 0.2% by weight, calculated based on the total composition, of an alkali magnesium chlorophyllin, an alkali copper chlorophyllin, or a mixture thereof to human hair.

6. The composition according to claim 1, wherein said reducing agent is selected from the group consisting of a thioglycolic acid salt, glycerol monothioglycollate, thiolactic acid, and esters and inorganic sulfites thereof.

7. The composition according to claim 3, wherein said alkali magnesium chlorophyllin is selected from the group consisting of sodium magnesium chlorophyllin and potassium magnesium chlorophyllin.

* * * * *